United States Patent
Scholz et al.

(10) Patent No.: US 7,179,946 B2
(45) Date of Patent: Feb. 20, 2007

(54) COPPER COMPLEXES AND THEIR USE

(75) Inventors: Ulrich Scholz, Mülheim (DE); Klaus Kunz, Düsseldorf (DE); Oliver Gaertzen, Köln (DE); Jordi Benet-Buchholz, Leverkusen (DE); Joachim Wesener, Köln (DE)

(73) Assignee: Lanxess Deutschland GmbH, Leverkusen (DE)

( * ) Notice: Subject to any disclaimer, the term of this patent is extended or adjusted under 35 U.S.C. 154(b) by 467 days.

(21) Appl. No.: 10/752,413

(22) Filed: Jan. 6, 2004

(65) Prior Publication Data

US 2004/0198997 A1    Oct. 7, 2004

(30) Foreign Application Priority Data

Jan. 7, 2003    (DE) ................ 103 00 097

(51) Int. Cl.
| | |
|---|---|
| *C07C 319/00* | (2006.01) |
| *C07C 209/00* | (2006.01) |
| *C07C 41/00* | (2006.01) |
| *B01J 31/00* | (2006.01) |
| *C07F 1/08* | (2006.01) |

(52) U.S. Cl. ............... 568/38; 568/630; 568/631; 568/659; 568/58; 564/161; 564/184; 564/404; 564/405; 556/13; 556/21; 556/22; 585/509

(58) Field of Classification Search ............ 556/13, 556/21, 22; 585/509; 568/38, 58, 630, 631, 568/659; 564/161, 184, 404, 405
See application file for complete search history.

(56) References Cited

U.S. PATENT DOCUMENTS 4,319,050 A    3/1982   Doyle ................ 568/671

FOREIGN PATENT DOCUMENTS

| | | |
|---|---|---|
| DE | 24 31 330 | 1/1976 |
| EP | 679 438 | 11/1995 |
| WO | 03/078418 | 3/2003 |

OTHER PUBLICATIONS

Quiros M et al: "Enantioselective reduction of beta-keto amides by the fungus *Mortierella isabellina*" Tetrahedron: Asymmetry, Elsevier Science Publishers, Amsterdam, NL. Bd 8, Nr. 18, Sep. 25, 1997, Seiten 3035-3038, XP004090508 ISSN: 0957-4166 "Zusammenfassung" Tabelle 1, Produkt 2a-c.

Delhi J R et al: "Enantio- and chemoselective bioreduction of beta-keto nitriles by the fungus *Curvularia lunata*" Tetrahedron: Asymmetry, Elsevier Science Publishers, Amsterdam, NL, Bd. 11, Nr. 18, Sep. 22, 2000, Seiten 3693-3700, XP004219718 ISSN: 0957-4166 "Zusammenfassung" Tabelle 1, Produkt 2b.

Tetrahedron Letters, 2001, 42, 4791-4793, "Formation of aryl-nitrogen bonds using a soluble copper(I) catalyst", D. Venkataraman et al.

Netherton, M. R.; Fu, G. C.; Organic Letters (2001), 3(26), 4295-4298, "Air-Stable Trialkylphos-phonium Salts: Simple, Practical, and Versatile Replacements for Air-Sensitive Trialkylphosphines. Applications in Stoichiometric and Catalytic Processes".

Inorganic Chemistry (2000), 39(22), 5121-5132, Coden: INOCAJ; ISSN: 0020-1669, American Chemical Society, Graham, Peter M. et al "Coordination Polymers of Copper(I) Halides" XP-002277655.

Tetrahedron Letters. vol. 25, No. 37, pp. 4087-4090, 1984, 0040-4039. "Influence of Olefin Coordination on Cyclopropanation Selectivity", Michael P. Doyle, et al XP002277654.

*Primary Examiner*—Porfirio Nazario-Gonzalez
(74) *Attorney, Agent, or Firm*—Michael A. Miller

(57) ABSTRACT

The invention relates to copper complexes of phosphorus compounds, to a process for their preparation and to their use in catalytic coupling reactions.

7 Claims, No Drawings

COPPER COMPLEXES AND THEIR USE

BACKGROUND OF THE INVENTION

1. Field of the Invention

The invention relates to copper complexes of phosphorus compounds, to a process for their preparation and to their use in catalytic coupling reactions.

2. Brief Description of the Prior Art

Coupling reactions catalyzed by copper complexes of aryl halides or arylsulphonates with heteroatom functionalities, for example thiols, amines and amides, have been described in the literature.

Ligands thereof comprising oxygen or phosphorus compounds are frequently used. For example, Venkataraman et al. (Tetrahedron Letters, 2001, 42, 4791–4793) disclose the use of preformed complexes of copper dibromide and triphenylphosphine to add aryl halides to secondary aromatic amines.

However, disadvantages of the copper complexes of phosphorus compounds known hitherto are the often low chemoselectivity and the narrow spectrum of reactions in which industrially acceptable conversions and conversion rates can be achieved.

There is, therefore, a need to provide copper complexes of phosphorus compounds which are easy to prepare and afford the desired products in good yields in coupling reactions.

SUMMARY OF THE INVENTION

The present invention therefore provides compounds of the formula (I)

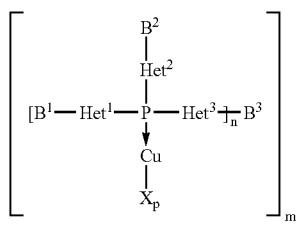

in which

Het$^1$, Het$^2$ and Het$^3$ are each independently absent, or are oxygen or NR$^1$ where R$^1$ is C$_1$–C$_8$-alkyl, C$_5$–C$_{18}$-aryl or C$_6$–C$_{19}$-arylalkyl and B$^1$ and B$^2$ are each independently C$_1$–C$_8$-alkyl, C$_5$–C$_{18}$-aryl or C$_6$–C$_{19}$-arylalkyl, or the B$^1$ and B$^2$ radicals together may be a divalent radical having a total of 2 to 40 carbon atoms and B$^3$ is C$_1$–C$_8$-alkyl, C$_5$–C$_{18}$-aryl, C$_6$–C$_{19}$-arylalkyl or a radical having a total of 2 to 40 carbon atoms and the valency n, X is halide, (C$_1$–C$_8$-haloalkyl)carboxylate, (C$_1$–C$_8$-alkyl)carboxylate, (C$_1$–C$_8$-haloalkyl)sulphonate, (C$_5$–C$_{18}$-aryl)sulphonate, cyanide, optionally fluorinated acetylacetonate, nitrate, oxinate, phosphate, carbonate, hexafluorophosphate, tetraphenylborate, tetrakis-(pentafluorophenyl)borate or tetrafluoroborate, and p is 0, 1 or 2 and n is 1, 2 or 3 and m is 1, 2, 3, 4, 5 or 6.

In the context of the invention, all of the radical definitions, parameters and illustrations above and listed hereinbelow, in general or within areas of preference, i.e. the particular areas and areas of preference too, may be combined as desired.

DETAILED DESCRIPTION OF THE INVENTION

Alkyl, alkoxy, alkylene and alkenylene are each independently a straight-chain, cyclic, branched or unbranched alkyl, alkoxy, alkylene and alkenylene radical respectively, and each of the radicals mentioned may optionally also be substituted by C$_1$–C$_4$-Alkoxy. The same applies to the nonaromatic moiety of an aralkyl radical.

C$_1$–C$_4$-Alkyl is, for example, methyl, ethyl, n-propyl, isopropyl, n-butyl, sec-butyl and tert-butyl, C$_1$–C$_8$-alkyl is additionally, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, 1-ethyl-2-methylpropyl, n-heptyl and n-octyl, C$_1$–C$_{12}$-alkyl is further additionally, for example, adamantyl, the isomeric menthyls, n-nonyl, n-decyl and n-dodecyl, and C$_1$–C$_{18}$-alkyl is still further additionally, for example, n-octadecyl.

C$_1$–C$_4$-Alkoxy is, for example, methoxy, ethoxy, n-propoxy, isopropoxy, n-butoxy, sec-butoxy and tert-butoxy, C$_1$–C$_8$-alkoxy is additionally n-pentoxy, 1-methylbutoxy, 2-methylbutoxy, 3-methylbutoxy, neopentoxy, 1-ethylpropoxy, cyclohexoxy, cyclopentoxy, n-hexoxy and n-octoxy, and C$_1$–C$_{12}$-alkoxy is further additionally, for example, adamantoxy, the isomeric menthoxy radicals, n-decoxy and n-dodecoxy.

C$_1$–C$_8$-Alkylene is, for example, methylene, 1,1-ethylene, 1,2-ethylene, 1,1-propylene, 1,3-propylene, 1,4-butylene, 1,2-cyclohexoxylene and 1,2-cyclopentylene.

Haloalkyl is in each case independently a straight-chain, cyclic, branched or unbranched alkyl radical which is singly, multiply, or fully substituted by chlorine or fluorine atoms. C$_1$–C$_8$-haloalkyl is, for example, trifluoromethyl, chlorodifluoromethyl, 2,2,2-trifluoroethyl, pentafluoroethyl, nonafluorobutyl, heptafluoroisopropyl and perfluorooctyl.

Aryl is in each case independently a heteroaromatic radical having 5 to 18 framework carbon atoms of which no, one, two or three framework carbon atoms per cycle, but at least one framework carbon atom in the entire molecule, may be substituted by heteroatoms selected from the group of nitrogen, sulphur or oxygen, but is preferably a carbocyclic aromatic radical having 6 to 18 framework carbon atoms.

Examples of carbocyclic aromatic radicals having 6 to 18 framework carbon atoms are phenyl, naphthyl, phenanthrenyl, anthracenyl or fluorenyl, and heteroaromatic radicals having 5 to 14 framework carbon atoms of which no, one, two or three framework carbon atoms per cycle, but at least one framework carbon atom in the entire molecule, may be substituted by heteroatoms selected from the group of nitrogen, sulphur or oxygen are, for example, pyridinyl, oxazolyl, benzofuranyl, dibenzofuranyl or quinolinyl.

The carbocyclic aromatic radical or heteroaromatic radical may also be substituted by up to five identical or different substituents per cycle which are selected from the group of free or protected hydroxyl, cyano, chlorine, fluorine, $C_1C_{12}$–alkyl, $CO(C_1$–$C_{12}$-alkyl), $COO(C_1$–$C_{12}$-alkyl), $CO(C_5$–$C_{18}$-aryl), $COO(C_5$–$C_{18}$-aryl), $CON(C_1$–$C_{12}$-alkyl)$_2$, $C_5$–$C_{18}$-aryl, $C_1$–$C_{12}$-haloalkyl, $C_1$–$C_{12}$-alkoxy, $C_1$–$C_{12}$-haloalkoxy, di($C_1$–$C_8$-alkyl)amino or tri($C_1$–$C_6$-alkyl)siloxyl.

Arylalkyl is in each case independently a straight-chain, cyclic or branched or unbranched alkyl radical as defined above which may be singly, multiply or fully substituted by aryl radicals as defined above.

The preferred substitution patterns are defined hereinbelow:

$Het^1$, $Het^2$ and $Het^3$ are preferably each independently oxygen or are absent, $B^1$ and $B^2$ are preferably each independently secondary $C_3$–$C_8$-alkyl or tertiary $C_4$–$C_8$-alkyl, $C_5$–$C_{18}$-aryl or bis($C_5$–$C_{19}$-aryl), or $B^1$ and $B^2$ together are a divalent radical which is selected from the group of 1,2-phenylene, 1,3-phenylene, 1,2-cyclohexyl, 1,1'-ferrocenyl, 1,2-ferrocenyl, 2,2'-(1,1'-binaphthyl) and 1,1'-biphenyl, and the radicals mentioned may optionally be mono- or polysubstituted by cyano, chlorine, fluorine, $C_1$–$C_{12}$-alkyl, $C_1$–$C_{12}$-haloalkyl, $C_1$–$C_{12}$-alkoxy, $C_1$–$C_{12}$-haloalkoxy, di($C_1$–$C_8$-alkyl)amino or tri($C_1$–$C_8$-alkyl)siloxyl, $B^3$ is preferably secondary $C_3$–$C_8$-alkyl or tertiary $C_4$–$C_8$-alkyl, $C_5$–$C_{18}$-aryl, $C_6$–$C_{19}$-arylalkyl or a radical having a total of from 2 to 40 carbon atoms and the valency n, X is preferably chloride, bromide or iodide, trifluoromethanesulphonate, trifluoroacetate, methanesulphonate, benzenesulphonate, cyanide, optionally fluorinated acetylacetonate, hexafluorophosphate or tetrafluoroborate, and particular preference is given to chloride, bromide or iodide.

n is preferably 1 or 2, m is preferably 1 or 2.

It has been found that a ratio of copper to phosphorus atoms in the complex, as illustrated by formula (I), can be attained very easily or automatically especially when the ligand contains at least one poly($C_5$–$C_{18}$)aryl or ($C_9$–$C_{18}$) aryl structural element or, as a structural element, at least one ($C_5$–$C_{18}$)aryl structural element substituted in the ortho-position by secondary or tertiary alkyl, or, in the case of ligands which contain more than one phosphorus atom, $B^3$ is not 1,1'-bisarylene, 2,2'-bisarylene, 1,2-arylene or 1,2-, 1,3- or 1,4-($C_1$–$C_8$)alkylene.

In the present embodiment of the invention, formula (I) includes in particular copper-phosphine complexes, copper-phosphonite complexes and copper-phosphite complexes.

Preferred copper-phosphine complexes are, for example, those which contain the following phosphine ligands:

Bis(2-dicyclohexylphosphino)-2'-(N,N-dimethylamino) biphenyl, 2-(dicyclohexylphosphino)biphenyl, 2-(dicyclohexylphosphino)-2'-methylbiphenyl, 2-(di-tert-butylphosphino)biphenyl or 2-(bisdiphenylphosphino)binaphthyl.

Preference is given to 2-(di-tert-butylphosphino)biphenyl or 2-(dicyclohexylphosphino)biphenyl.

Particularly preferred copper-phosphine complexes are $[(\mu-Br)_2\{2-(di-tert-butylphosphino)biphenyl\}_2Cu_2]$, $[(\mu-trifluoromethanesulphonato)_2\{2-(di-tert-butylphosphino) biphenyl\}_2Cu_2]$, $[(\mu-Br)_2\{2-(dicyclohexylphosphino)biphen-yl\}_2Cu_2]$ and $[(\mu-trifluoromethanesulphonato)_2\{2-(dicyclohexylphosphino)-biphenyl\}_2Cu_2]$.

Preferred copper-phosphonite complexes are, for example, those which contain the following phosphonite ligands:

1,1'-Biphenyl-2-yl dialkyl phosphonites, for example and with preference 1,1'-biphenyl-2-yl dicyclohexyl phosphonite and 1,1'-biphenyl-2-yl di-tert-butyl phosphonite, 3-[(diisopropylphosphino)oxy]phenyl diisopropyl phosphonite, 3-[(di-tert-butylphosphino)oxy]phenyl di-tert-butyl phosphonite, 3-[(diphenylphosphino)oxy]phenyl diphenyl phosphonite or 3-[(dicyclohexylphosphino)oxy]phenyl dicyclohexyl phosphonite, and even greater preference is given to 3-[(diisopropylphosphino)oxy]phenyl diisopropyl phosphonite.

A particularly preferred copper-phosphonite complex is $[(\mu-Br)_2\{2-(di-tert-butylphosphino)biphenyl\}_2Cu_2]$.

Preferred copper-phosphite complexes are, for example, those which contain the following phosphite ligands:

1,1'-Binaphthyl-2,2'-diyl isopropyl phosphite, 2,4,8,10-tetra-tert-butyl-6-phenoxy-12H-dibenzo[d,g][1,3,2]dioxaphosphocine, and particular preference is given to 1,1'-binaphthyl-2,2'-diyl isopropyl phosphite and tris(2,4-di-tert-butylphenyl) phosphite.

A particularly preferred copper-phosphite complex is $[(\mu-Br)_2\{1,1'-binaphthyl-2,2'-diyl\ isopropyl\ phosphite\}_2Cu_2]$.

The copper phosphorus complexes of the formula (I) according to the invention can be prepared, for example, in a manner known per se by reacting phosphorus compounds of the formula (II)

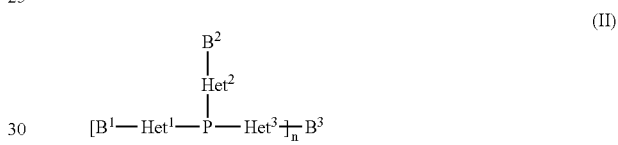

(II)

in which n, $B^1$, $B^2$, $B^3$, $Het^1$, $Het^2$ and $Het^3$ each have the definitions and areas of preference specified under the formula (I) with compounds of the formula (III)

(III)

in which X and p each have the definitions and areas of preference specified in the formula (I).

In cases in which p=0, copper powder, for example, can also be used.

Preferred compounds of the formula (III) are:

Copper(I) oxide, copper(II) oxide, copper(I) chloride, copper(I) trifluoromethanesulphonate, copper(I) bromide, copper(I) iodide, copper(II) bromide, copper(II) chloride, copper(II) acetate, copper(II) acetylacetonate or mixtures thereof.

The molar ratio of phosphorus atoms in compounds of the formula (II) to copper atoms in compounds of the formula (III) in the preparation of complexes of the formula (I) may generally be 10:1 to 0.5:1, preferably 2:1 to 1:1, more preferably 1.2:1 to 1:1.

The compounds of the formula (I) can be prepared separately in an inert organic solvent suitable for this purpose, for example tetrahydrofuran, diethyl ether, toluene, xylene, chloroform, dichloromethane, methanol and/or ethanol.

The most favourable amount of solvent to be used can be determined by appropriate preliminary experiments.

The compounds of the formula (I) are prepared from the starting compounds of the formulae (II) and (III) described, for example, by simply combining the two starting compounds in solution at room temperature.

It is also possible to prepare the compounds of the formula (I) in situ in a catalysis mixture. For this purpose, the compounds of the formula (II) can also be used in the form of phosphonium salts, for example tetrafluoroborates (see also Netherton, M. R.; Fu, G. C.; Organic Letters (2001), 3(26), 4295–429).

The inventive compounds of the formula (I) are suitable in particular for forming carbon-nitrogen, carbon-oxygen and carbon-sulphur bonds, and also for preparing arylalkines.

The invention also encompasses catalysts which comprise compounds of the formula (I).

In addition, the invention also encompasses a process for preparing compounds of the formula (IV)

$$Ar-(F-R^2)_n \quad (IV)$$

in which
n is 1, 2 or 3 and
Ar is a substituted or unsubstituted aromatic radical and
F is oxygen, sulphur, $NR^3$, $NR^3CO$ or ethyndiyl, where $R^3$ is hydrogen, $C_1$–$C_{12}$-alkyl, $C_5$–$C_{18}$-aryl or $C_6$–$C_{19}$-arylalkyl and
$R^2$ is Ar, $C_1$–$C_{12}$-alkyl, $C_1$–$C_{12}$-haloalkyl, $C_2$–$C_{12}$-alkenyl or $C_6$–$C_{19}$-arylalkyl, which is characterized in that compounds of the formula (V)

$$Ar-Z \quad (V)$$

in which
Ar is as defined above and
Z is chlorine, bromine, iodine, a diazonium salt or sulphonate are reacted with compounds of the formula (VI)

$$H-F-R^2 \quad (VI)$$

in which
F and $R^2$ are each as defined above and the conversion is effected in the presence of base and compounds of formula (I).

The areas of preference for compounds of the formulae (IV) to (VI) are defined hereinbelow:

Ar is preferably carbocyclic aromatic radicals having 6 to 24 framework carbon atoms or heteroaromatic radicals having 5 to 24 framework atoms of which no, one, two or three framework atoms per cycle, but at least one framework atom in the entire molecule, are heteroatoms which are selected from the group of nitrogen, sulphur and oxygen. The carbocyclic aromatic radicals or the heteroaromatic radicals may also be substituted by up to five identical or different substituents per cycle which are selected from the group of hydroxyl, chlorine, fluorine, nitro, cyano, free or protected formyl, $C_1$–$C_{12}$-alkyl, $C_5$–$C_{14}$-aryl, $C_6$–$C_{15}$-arylalkyl, —PO-[($C_1$–$C_8$)-alkyl]$_2$, —PO-[($C_5$–$C_{14}$)-aryl]$_2$, —PO-[($C_1$–$C_8$)-alkyl)($C_5$–$C_{14}$) aryl)], tri($C_1$–$C_8$-alkyl)siloxyl or radicals of the formula (VIIa–f)

A-B-D-E (VIIa)

A-E (VIIb)

A-SO$_2$-E (VIIc)

A-B—SO$_2$R$^4$ (VIId)

A-SO$_3$W (VIIe)

A-COW (VIIf)

in which, each independently,
A is absent or is a $C_1$–$C_8$-alkylene radical and
B is absent or is oxygen, sulphur or $NR^4$,
  where $R^4$ is hydrogen, $C_1$–$C_8$-alkyl, $C_6$–$C_{15}$-arylalkyl or $C_5$–$C_{14}$-aryl and
D is a carbonyl group and
E is $R^5$, $OR^5$, $NHR^6$ or $N(R^6)_2$,
  where $R^5$ is $C_1$–$C_8$-alkyl, $C_6$–$C_{15}$-arylalkyl, $C_1$–$C_8$-haloalkyl or $C_5$–$C_{14}$-aryl and
  $R^6$ is in each case independently $C_1$–$C_8$-alkyl, $C_6$–$C_{15}$-arylalkyl or $C_5$–$C_{14}$-aryl, or $N(R^6)_2$ together is a cyclic amino radical and
W is OH, NH$_2$ or OM where M may be an alkali metal ion, half an equivalent of an alkaline earth metal ion, an ammonium ion or an organic ammonium ion,
Ar is more preferably phenyl, naphthyl, phenanthrenyl, anthracenyl, biphenyl, binaphthyl, fluorenyl, pyridinyl, oxazolyl, thiophenyl, benzofuranyl, benzothiophenyl, dibenzofuranyl, dibenzothiophenyl, furanyl, indolyl, pyridazinyl, pyrazinyl, pyrimidinyl, triazolyl and quinolinyl, and the radicals mentioned may also be substituted by no, one, two or three radicals per cycle, each of which is selected independently from the group of fluorine, nitro, cyano, di($C_1$–$C_4$-alkyl)amino, $C_1$–$C_4$-alkyl, $C_5$–$C_{10}$-aryl, $C_1$–$C_8$-fluoroalkyl, $C_1$–$C_8$-fluoroalkoxy, $C_1$–$C_8$-alkoxy, CO($C_1$–$C_4$-alkyl), COO-($C_1$–$C_4$)alkyl, —CON($C_1$–$C_4$-alkyl)$_2$,
Ar is even more preferably a phenyl radical which may be further substituted by no, one, two or three radicals, each of which is selected independently from the group of nitro, fluorine, cyano, $C_1$–$C_4$-alkyl, $C_1$–$C_4$-alkoxy, trifluoromethyl, trifluoromethoxy, CO-($C_1$–$C_4$)-alkyl, COO-($C_1$–$C_4$)-alkyl and —CON($C_1$–$C_4$-alkyl)$_2$,
n is preferably 1,
Z is preferably chlorine, bromine or iodine,
F is preferably oxygen, sulphur, $NR^3$ or ethindiyl, where $R^3$ is hydrogen, $C_1$–$C_4$-alkyl or $C_5$–$C_{18}$-aryl,
$R^2$ is preferably Ar or $C_1$–$C_{12}$-alkyl.

For the process according to the invention, the compounds of the formula (I) are generally used in amounts of 0.02 mol % to 10 mol %, preferably 0.1 mol % to 3 mol %, based on the compounds of the formula (IV) used.

The bases used in the process according to the invention are, for example and with preference alkali metal and/or alkaline earth metal carbonates, hydrogencarbonates, alkoxides, phosphates, fluorides and/or hydroxides, and mention should be made in particular of potassium carbonate and/or sodium carbonate, caesium carbonate, caesium hydrogencarbonate, sodium methoxide, potassium tert-butoxide, potassium amylate, caesium fluoride, potassium phosphate and barium hydroxide. Preference is given to using potassium carbonate, sodium carbonate, caesium carbonate and/or caesium hydrogencarbonate.

Particular preference is given to using potassium carbonate.

Per mole of Hal in compounds of the formula (IV) to be exchanged, for example, 0.05 to 10 mol of base can be used, preferably 0.3 to 2 mol.

It is advantageous for the process according to the invention when the bases used are pretreated by grinding and/or drying.

After the grinding, the specific surface areas of the bases are preferably from approx. 0.1 to 10 m$^2$/g, more preferably from 0.2 to 1 m$^2$/g (BET).

As a consequence of the marked hygroscopic properties of the bases used in the process according to the invention, the phosphates and carbonates in particular tend to absorb, to a greater or lesser extent, atmospheric constituents such as water and carbon dioxide. From an absorption of approx. 30 percent by weight of atmospheric constituents, a distinct influence on the conversions to be achieved can be detected. It is therefore frequently appropriate to dry the bases in addition to the grinding.

Depending on the nature of the bases used, the bases are dried, for example, by heating them to temperatures of approx. 50 to 200° C., preferably 100 to 160° C., under a reduced pressure of approx. 0.01 to 100 bar for several hours.

The molar ratio of compounds of the formula (VI) to compounds of the formula (IV) may be, for example, 0.8 to 10, preferably 1 to 6 and more preferably 1 to 4.

The process according to the invention can be carried out, for example, at temperatures of 20 to 250° C., preferably 100 to 150° C. The optimum reaction temperatures depend in particular on the type of the starting product, of the catalyst and of the bases used, and can be determined by simple preliminary experiments.

The process according to the invention can be carried out either in the presence or in the absence of a suitable solvent. Useful solvents are, for example, aliphatic, alicyclic or aromatic hydrocarbons, for example benzine, benzene, toluene, xylene, petroleum ether, hexane, cyclohexane; ethers such as diethyl ether, diisopropyl ether, dioxane, tetrahydrofuran or ethylene glycol dimethyl ether or ethylene glycol diethyl ether; amides, for example N,N-dimethylformamide, N,N-dimethylacetamide, N-methylformanilide, N-methylpyrrolidone or hexamethylphosphoramide; esters such as methyl acetate or ethyl acetate, or mixtures of such solvents.

In some cases, an excess of compounds of the formula (VI) can also serve as the reaction medium.

An azeotroping agent which continuously removes water formed in the course of the reaction azeotropically in the course of the distillation can optionally be added to the process according to the invention.

The process according to the invention can be carried out by customary methods in continuous or batchwise mode.

The advantage of the present invention is in particular the easy preparation of the compounds of the formula (I) and the high efficiency with which the inventive copper complexes can be used to prepare compounds of the formula (VI).

The invention is further described by the following illustrative but non-limiting examples.

EXAMPLES

Preparation of Compounds of the Formula (I)

Example 1

Preparation of bis(2-(di-tert-butylphosphino)biphenylcopper(I) bromide)

50 ml of degassed, anhydrous methanol were heated to reflux temperature, and 2.36 g (7.9 mmol) of 2-(di-tert-butylphosphino)biphenyl were added slowly to the methanol until the phosphine compound was completely dissolved. Subsequently, 0.59 g (2.6 mmol) of copper(II) bromide was added to the solution in portions. After the copper bromide had been added, the solution was heated to reflux temperature for a further 15 min, and then the solution was cooled. After the solution had been cooled, a solid precipitated out and was filtered off, and was washed with a little ethanol and diethyl ether and subsequently dried. 0.93 g (1.1 mmol) of the abovementioned compound was obtained. The yield was 80% of theory.

Example 2

Preparation of bis(N-[2'-(dicyclohexylphosphino)-1,1'-biphenyl-2-yl]-N,N-dimethylaminecopper(I) bromide) dimer 50 ml of degassed, anhydrous methanol were heated to reflux temperature, and 2.00 g (5.1 mmol) of N-[2'-(dicyclohexylphosphino)-1,1'-biphenyl-2-yl]-N,N-dimethylamine were added slowly to the methanol until the phosphine compound was completely dissolved. Subsequently, 0.8 g (3.7 mmol) of copper(II) bromide was added to the solution in portions. After the copper bromide had been added, the solution was heated to reflux temperature for a further 15 min, and then the solution was cooled. After the solution had been cooled, a solid precipitated out and was filtered off, and was washed with a little ethanol and diethyl ether and subsequently dried. 1.5 g (1.4 mmol, M=1073.8 g/mol) of the abovementioned compound were obtained. The structure was checked by an FD-MS analysis (m/e=1074). The yield was 73% of theory.

Example 3

Preparation of (3-[(diphenylphosphino)oxy]phenyl diphenyl phosphonite)copper(I) chloride In a round-bottomed flask, 5 g (10.4 mmol) of 3-[(diphenylphosphino)oxy]phenyl diphenyl phosphonite are dissolved in degassed, anhydrous dichloromethane and heated to 40° C. 0.35 g of copper(I) chloride (0.35 mmol) is added. After 30 minutes of stirring, the solvent is removed under reduced pressure. The above-mentioned compound was obtained.

Example 4

Preparation of bis-[(1,1'-biphenyl-2-yl dicyclohexyl phosphonite)copper(I) chloride]

In a round-bottomed flask, 5 g (13.6 mmol) of 1,1'-biphenyl-2-yl dicyclohexyl phosphonite are dissolved in anhydrous, degassed chloroform. In an argon countercurrent, 0.45 g (4.5 mmol) of copper(I) chloride is added and the mixture is stirred at room temperature for 6 hours. The solvent is removed under reduced pressure and the residue taken up in anhydrous ether. The mixture is cooled to −78° C. and the product precipitates out.

Example 5

Preparation of bis[4-isopropoxydinaphtho[2,1-d:1',2'-f][1,3,2]dioxaphosphepine]copper(I) chloride In a round-bottomed flask, 5 g (13.4 mmol) of 4-isopropoxydinaphtho[2,1-d:1',2'-f][1,3,2]dioxaphosphepine (rac-binaphthyl isopropyl phosphite) are dissolved in dichloromethane and 0.44 g (0.45 mmol) of copper(I) chloride is added in an argon countercurrent. After 30 minutes of stirring, the solvent is removed under reduced pressure.

Examples 6 to 24

Use of the catalysts of examples 1 and 2 in coupling reactions

Example 6

Coupling of p-bromoacetophenone with n-octanethiol (Catalyst from Example 1)

1.35 g (6.7 mmol) of p-bromoacetophenone, 1.0 g (6.7 mmol) of n-octanethiol, 1.8 g (13.5 mmol) of potassium carbonate and 300 mg (0.7 mmol) of the catalyst from example 1 are stirred in 50 ml of dioxane under an argon atmosphere at 110° C. for 12 h. The reaction solution is subsequently admixed with 40 ml of aqueous ammonia and extracted with ethyl acetate, and the combined organic extracts are dried under reduced pressure. After workup by column chromatography (hexane), 1.24 g (70%) of product are obtained.

GC-MS/EI: 264 (M)

Example 7

Coupling of p-bromoacetophenone with n-octanethiol (Catalyst from Example 2)

1.35 g (6.7 mmol) of p-bromoacetophenone, 1.0 g (6.7 mmol) of n-octanethiol, 1.8 g (13.5 mmol) of potassium carbonate and 360 mg (0.7 mmol) of the catalyst from example 2 are stirred in 50 ml of dioxane under an argon atmosphere at 110° C. for 12 h. The reaction solution is subsequently admixed with 40 ml of aqueous ammonia and extracted with ethyl acetate, and the combined organic extracts are dried under reduced pressure. After workup by column chromatography (hexane), 733 mg (40%) of product are obtained.

Example 8

Coupling of p-bromoacetophenone with Thiophenol (Catalyst from Example 1)

1.35 g (6.7 mmol) of p-bromoacetophenone, 0.75 g (6.7 mmol) of thiophenol, 1.8 g (13.5 mmol) of potassium carbonate and 300 mg (0.7 mmol) of the catalyst from example 1 are stirred in 50 ml of dioxane under an argon atmosphere at 110° C. for 12 h. The reaction solution is subsequently admixed with 20 ml of aqueous ammonia and extracted with ethyl acetate, and the combined organic extracts are dried under reduced pressure. After workup by column chromatography (hexane), 970 mg (65%) of product are obtained.

GC-MS/EI: 228 (M)

Example 9

Coupling of p-bromoacetophenone with Thiophenol (Catalyst from Example 2)

1.35 g (6.7 mmol) of p-bromoacetophenone, 0.75 g (6.7 mmol) of thiophenol, 1.8 g (13.5 mmol) of potassium carbonate and 360 mg (0.7 mmol) of the catalyst from example 2 are stirred in 50 ml of dioxane under an argon atmosphere at 110° C. for 12 h. The GC analysis of the crude product indicates product formation with 75% conversion.

Example 10

Coupling of p-bromoacetophenone with Phenol (Catalyst from Example 1)

1.35 g (6.7 mmol) of p-bromoacetophenone, 630 mg (6.7 mmol) of phenol, 1.8 g (13.5 mmol) of potassium carbonate and 300 mg (0.7 mmol) of the catalyst from example 1 are stirred in 50 ml of dioxane under an argon atmosphere at 110° C. for 12 h. The reaction solution is subsequently admixed with 40 ml of aqueous ammonia and extracted with ethyl acetate, and the combined organic extracts are dried under reduced pressure. After workup by column chromatography (hexane), 280 mg (20%) of product are obtained.

GC-MS/EI: 212

Example 11

Coupling of p-bromoacetophenone with Phenol (Catalyst from Example 2)

1.35 g (6.7 mmol) of p-bromoacetophenone, 630 mg (6.7 mmol) of phenol, 1.8 g (13.5 mmol) of potassium carbonate and 360 mg (0.7 mmol) of the catalyst from example 2 are stirred in 50 ml of dioxane under an argon atmosphere at 110° C. for 12 h. The GC analysis of the crude product indicates product formation with 18% conversion.

Example 12

Coupling of p-bromoacetophenone with 2-hydroxypyridine (Catalyst from Example 1)

1.35 g (6.7 mmol) of p-bromoacetophenone, 650 mg (6.7 mmol) of 2-hydroxypyridine, 1.8 g (13.5 mmol) of potassium carbonate and 300 mg (0.7 mmol) of the catalyst from example 1 are stirred in 50 ml of dioxane under an argon atmosphere at 110° C. for 12 h. The reaction solution is subsequently admixed with 40 ml of aqueous ammonia and extracted with ethyl acetate, and the combined organic extracts are dried under reduced pressure. After workup by column chromatography (hexane), 740 mg (52%) of a product mixture of N4-acetylphenylpyridinone and 4-acetylphenoxy-2-pyridine (ratio 6:1) are obtained.

GC-MS/EI: 213 (M)

Example 13

Coupling of p-bromoacetophenone with 2-hydroxypyridine (Catalyst from Example 2)

1.35 g (6.7 mmol) of p-bromoacetophenone, 650 mg (6.7 mmol) of o-hydroxypyridine, 1.8 g (13.5 mmol) of potassium carbonate and 360 mg (0.7 mmol) of the catalyst from example 2 are stirred in 50 ml of dioxane under an argon atmosphere at 110° C. for 12 h. The GC analysis of the crude product indicates product formation with 42% conversion.

Example 14

Coupling of p-bromoacetophenone with Methanol (Catalyst from Example 1)

1.34 g (13.5 mmol) of p-bromoacetophenone, 2 ml (20 mmol) of ethyl acetate, 17.5 ml of a 30% sodium methoxide solution and 300 mg (0.7 mmol) of the catalyst from example 1 are refluxed under an argon atmosphere for 12 h.

The reaction solution is subsequently hydrolyzed cautiously and extracted with dichloromethane, and the combined organic extracts are dried under reduced pressure. In addition to the product (35%) in a high proportion, the GC shows fragments of the aldol by-product. After workup by column chromatography (hexane), 820 mg (41%) of product were obtained.

GC-MS/EI: 150 (M)

Example 15

Coupling of p-bromoacetophenone with Methanol (Catalyst from Example 2)

1.34 g (13.5 mmol) of p-bromoacetophenone, 2 ml (20 mmol) of ethyl acetate, 17.5 ml of a 30% sodium methoxide solution and 360 mg (0.7 mmol) of the catalyst from example 2 are refluxed under an argon atmosphere for 12 h. The reaction solution is subsequently hydrolysed cautiously and extracted with dichloromethane, and the combined organic extracts are dried under reduced pressure. In addition to the product (28%) in a high proportion, the GC shows fragments of the aldol by-product.

Example 16

Coupling of 4-iodotrifluoromethylbenzene with Phenylacetylene (Catalyst from Example 1)

2.7 g (10 mmol) of 4-iodotrifluoromethylbenzene, 1.3 g (12.5 mmol) of phenylacetylene, 2.2 g (20 mmol) of potassium tert-butoxide and 300 mg (0.7 mmol) of the catalyst from example 1 are stirred in 100 ml of dioxane under an argon atmosphere at 110° C. for 21 h. The reaction solution is filtered and dried under reduced pressure. After workup by column chromatography (hexane), 1.88 g (75%) of product are obtained.

GC-MS/EI: 246 (M)

Example 17

Coupling of 4-iodotrifluoromethylbenzene with Phenylacetylene (Catalyst from Example 2)

2.7 g (10 mmol) of 4-iodotrifluoromethylbenzene, 1.3 g (12.5 mmol) of phenylacetylene, 2.2 g (20 mmol) of potassium tert-butoxide and 360 mg (0.7 mmol) of the catalyst from example 2 are stirred in 100 ml of dioxane under an argon atmosphere at 110° C. for 21 h. The GC analysis of the crude product indicates product formation (cf. with GC-MS/EI GZN 283-4) with 62% conversion.

Example 18

Coupling of p-tolyl Iodide with Phenylacetylene (Catalyst from Example 1)

2.2 g (10 mmol) of p-tolyl iodide, 1.3 g (12.5 mmol) of phenylacetylene, 2.2 g (20 mmol) of potassium tert-butoxide and 300 mg (0.7 mmol) of the catalyst from example 1 are stirred in 100 ml of dioxane under an argon atmosphere at 110° C. for 21 h. The reaction solution is filtered and dried under reduced pressure. After workup by column chromatography (hexane), 1.75 g (91%) of product are obtained.

GC-MS/EI: 192 (M)

Example 19

Coupling of p-tolyl Iodide with Phenylacetylene (Catalyst from Example 2)

2.2 g (10 mmol) of p-tolyl iodide, 1.3 g (12.5 mmol) of phenylacetylene, 2.2 g (20 mmol) of potassium tert-butoxide and 360 mg (0.7 mmol) of the catalyst from example 2 are stirred in 100 ml of dioxane under an argon atmosphere at 110° C. for 21 h. The GC analysis of the crude product indicates product formation (cf. with GC-MS/EI GZN 277-8) with 50% conversion.

Example 20

Coupling of Bromobenzene with Aniline (Catalyst from Example 1)

1.05 g (6.7 mmol) of bromobenzene, 1.4 g (10.1 mmol) of caesium carbonate and 300 mg (0.7 mmol) of the catalyst from example 1 are stirred in 2 ml of aniline under an argon atmosphere at 170° C. for 12 h.

The GC analysis of the crude product indicates the selective formation of the monoarylated compound GC-MS/EI: 169; (M)) and a conversion of 5%; triarylamine is not detected.

Example 21

Coupling of Iodobenzene with Aniline (Catalyst from Example 1)

1.37 g (6.7 mmol) of iodobenzene, 1.4 g (10.1 mmol) of caesium carbonate and 300 mg (0.7 mmol) of the catalyst from example 1 are stirred in 2 ml of aniline under an argon atmosphere at 170° C. for 12 h. The GC analysis of the crude product indicates the selective formation of the monoarylated compound (cf. with GC-MS/EI of 1126-7; triarylamine is not detected. After workup by column chromatography, 810 mg (72%) of product are obtained.

Example 22

Coupling of p-chloronitrobenzene with Aniline (Catalyst from Example 1)

1.06 g (6.7 mmol) of p-chloronitrobenzene, 1.4 g (10.1 mmol) of caesium carbonate and 300 mg (0.7 mmol) of the catalyst from example 1 are stirred in 2 ml of aniline under an argon atmosphere at 170° C. for 12 h. The GC analysis of the crude product indicates the selective formation of the monoarylated compound and 83% conversion; triarylamine is not detected. After workup by column chromatography, 1.14 g (80%) of product are obtained.

GC-MS/EI: 214 (M)

Example 23

Coupling of Iodobenzene with Aniline (Catalyst from Example 2)

1.37 g (6.7 mmol) of iodobenzene, 1.4 g (10.1 mmol) of caesium carbonate and 360 mg (0.7 mmol) of the catalyst from example 2 are stirred in 2 ml of aniline under an argon atmosphere at 170° C. for 12 h. The GC analysis of the crude product indicates the selective formation of the monoarylated compound and complete conversion; triarylamine is not detected.

Example 24

Coupling of p-chloronitrobenzene with Aniline (Catalyst from Example 2)

1.06 g (6.7 mmol) of p-chloronitrobenzene, 1.4 g (10.1 mmol) of caesium carbonate and 360 mg (0.7 mmol) of the catalyst from example 2 are stirred in 2 ml of aniline under an argon atmosphere at 170° C. for 12 h. The GC analysis of the crude product indicates the selective formation of the monoarylated compound (comparison with GC-MS/EI of 1101-7) and 91% conversion; triarylamine is not detected.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a compound(s) of the formula (IV)

$$Ar-(F-R2)_n \qquad (IV)$$

in which
n is 1, 2 or 3 and
Ar is a substituted or unsubstituted aromatic radical and
F is oxygen, sulphur, $NR^3$, $NR^3CO$ or ethyndiyl, where $R^3$ is hydrogen, $C_1$–$C_{12}$-alkyl, $C_5$–$C_{18}$-aryl or $C_6$–$C_{19}$-arylalkyl and
$R^2$ is Ar, $C_1$–$C_{12}$-alkyl, $C_1$–$C_{12}$-haloalkyl, $C_2$–$C_{12}$-alkenyl or $C_6$–$C_{19}$-arylalkyl,
comprising reacting a compound(s) of the formula (V)

$$Ar-Z \qquad (V)$$

in which
Ar is as defined above and
Z is chlorine, bromine, iodine, a diazonium salt or sulphonate with a compound(s) of the formula (VI)

$$H-F-R^2 \qquad (VI)$$

in which
F and $R^2$ are each as defined above and
in the presence of base and a compound(s) of the formula (I)

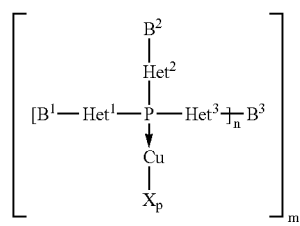

(I)

in which
$Het^1$, $Het^2$ and $Het^3$ are each independently absent, or are oxygen or $NR^1$ where $R^1$ is $C_1$–$C_8$-alkyl, $C_5$–$C_{18}$-aryl or $C_6$–$C_{19}$-arylalkyl and
$B^1$ and $B^2$ are each independently $C_1$–$C_8$-alkyl, $C_5$–$C_{18}$-aryl or $C_6$–$C_{19}$-arylalkyl, or the $B^1$ and $B^2$ radicals together are a divalent radical having a total of 2 to 40 carbon atoms and
$B^3$ is $C_1$–$C_8$-alkyl, $C_5$–$C_{18}$-alkyl, $C_6$–$C_{19}$-arylalkyl or a radical having a total of 2 to 40 carbon atoms and the valency n, Xis halide, ($C_1$–$C_8$-haloalkyl)carboxylate, ($C_1$–$C_8$-alkyl)carboxylate, ($C_1$–$C_8$-haloalkyl)sulphonate, ($C_5$–$C_{18}$-aryl)sulphonate, cyanide, optionally fluorinated acetylacetonate, nitrate, oxinate, phosphate, carbonate, hexafluorophosphate, tetraphenylborate, tetrakis(pentafluorophenyl)borate or tetrafluoroborate, and
p is 0, 1, or 2 and
n is 1, 2 or 3 and
m is 1, 2, 3, 4, 5 or 6.

2. The process according to claim 1, wherein the compound(s) according to the formula (I) is used as an isolated compound(s) or is generated in situ.

3. The process according to claim 1, wherein Ar is carbocyclic aromatic radicals having 6 to 24 framework carbon atoms or heteroaromatic radicals having 5 to 24 framework atoms of which zero, one, two or three framework atoms per cycle, but at least one framework atom in the entire molecule, are heteroatoms which are selected from the group of nitrogen, sulphur and oxygen, and the carbocyclic aromatic radicals or the heteroaromatic radicals which are optionally substituted by up to five identical or different substituents per cycle which are selected from the group of hydroxyl, chlorine, fluorine, nitro, cyano, free or protected formyl, $C_1$–$C_{12}$-alkyl, $C_5$–$C_{14}$-aryl, $C_6$–$C_{15}$-arylalkyl, —PO-[($C_1$–$C_8$)-alkyl]$_2$, —PO-[($C_5$–$C_{14}$)-aryl]$_2$, —PO-[($C_1$–$C_8$)-alkyl)($C_5$–$C_{14}$)aryl)], tri($C_1$–$C_8$-alkyl)siloxyl or radicals of the formula (VIIa–f)

$$A\text{-}B\text{-}D\text{-}E \qquad (VIIa)$$

$$A\text{-}E \qquad (VIIb)$$

$$A\text{-}SO_2\text{-}E \qquad (VIIc)$$

$$A\text{-}B\text{---}SO_2R^4 \qquad (VIId)$$

$$A\text{-}SO_3W \qquad (VIIe)$$

$$A\text{-}COW \qquad (VIIf)$$

in which, each independently,
A is absent or is a $C_1$–$C_8$-alkylene radical and
B is absent or is oxygen, sulphur or $NR^4$,
where $R^4$ is hydrogen, $C_1$–$C_8$-alkyl, $C_6$–$C_{15}$-arylalkyl or $C_5$–$C_{14}$-aryl and
D is a carbonyl group and
E is $R^5$, $OR^5$, $NHR^6$ or $N(R^6)_2$,
where $R^5$ is $C_1$–$C_8$-alkyl, $C_6$–$C_{15}$-arylalkyl, $C_1$–$C_8$-haloalkyl or $C_5$–$C_{14}$-aryl and
$R^6$ is in each case independently $C_1$–$C_8$-alkyl, $C_6$–$C_{15}$-arylalkyl or $C_5$–$C_{14}$-aryl, or $N(R^6)_2$ together is a cyclic amino radical and
W is OH, $NH_2$ or OM where M is an alkali metal ion, half an equivalent of an alkaline earth metal ion, an ammonium ion or an organic ammonium ion.

4. The process according to claim 1, wherein $R^2$ is Ar or $C_1$–$C_{12}$-alkyl.

5. The process according to claim 1, wherein the compound(s) of the formula (I) is used in amounts of 0.02 mol % to 10 mol %, based on the compounds of the formula (IV) used.

6. The process according to claim 1, wherein the base used is an alkali metal and/or alkaline earth metal carbonate, hydrogencarbonate, alkoxide, phosphate, fluoride and/or hydroxide.

7. The process according to claim 1, wherein the base used is pretreated by grinding and/or drying.

* * * * *